(12) United States Patent
Ohara (10) Patent No.: US 12,343,192 B2
(45) Date of Patent: Jul. 1, 2025

(54) RADIOGRAPHING CONTROL APPARATUS, RECORDING MEDIUM, AND RADIOGRAPHING SYSTEM

(71) Applicant: Konica Minolta, Inc., Tokyo (JP)

(72) Inventor: Hiromu Ohara, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 366 days.

(21) Appl. No.: 18/152,953

(22) Filed: Jan. 11, 2023

(65) Prior Publication Data

US 2023/0233172 A1 Jul. 27, 2023

(30) Foreign Application Priority Data

Jan. 21, 2022 (JP) .................................. 2022-007601

(51) Int. Cl.
*A61B 6/00* (2006.01)
*A61B 6/46* (2024.01)
*G06T 7/00* (2017.01)

(52) U.S. Cl.
CPC .............. *A61B 6/542* (2013.01); *A61B 6/465* (2013.01); *A61B 6/486* (2013.01); *A61B 6/541* (2013.01); *G06T 7/0012* (2013.01); *G06T 2207/10128* (2013.01); *G06T 2207/30061* (2013.01)

(58) Field of Classification Search
CPC ......... A61B 6/542; A61B 6/465; A61B 6/486; A61B 6/541; G06T 7/0012; G06T 2207/10128; G06T 2207/30061
See application file for complete search history.

(56) References Cited

U.S. PATENT DOCUMENTS

2020/0396395 A1* 12/2020 Kuwata .................... H04N 5/32
2025/0054141 A1*  2/2025 Takagi ................... G06T 7/0012

FOREIGN PATENT DOCUMENTS

| JP | 2010-172362 A | 8/2010 |
| JP | 5195907 B2 | 5/2013 |
| JP | 2021-112471 A | 8/2021 |

* cited by examiner

*Primary Examiner* — David P Porta
*Assistant Examiner* — Fani Polyzos Boosalis
(74) *Attorney, Agent, or Firm* — LUCAS & MERCANTI, LLP (57) ABSTRACT

A radiographing control apparatus emits radiation to an object and obtains a plurality of frame images to control dynamic radiographing that radiographs dynamics of the object. The radiographing control apparatus includes a hardware processor. The hardware processor obtains first order information that includes at least one of information on presence or absence of dynamic analysis executed for a dynamic image obtained by the dynamic radiographing, and information on a dynamic analysis item, determines a first radiographing condition and a target image quality, based on the obtained first order information, and determines a second radiographing condition for achieving the determined target image quality.

13 Claims, 8 Drawing Sheets

| FIRST ORDER INFORMATION | RADIOGRAPHING CONDITION A | | | | | TARGET IMAGE QUALITY | SECOND ORDER INFORMATION | RADIOGRAPHING CONDITION B | | |
|---|---|---|---|---|---|---|---|---|---|---|
| DYNAMIC ANALYSIS ITEM / PRESENCE OR ABSENCE OF DYNAMIC ANALYSIS | RESPIRATION PROTOCOL | RADIOGRAPHING POSTURE | SID (cm) | FRAME RATE (FPS) | RADIOGRAPHING TIME (sec) | TARGET S-VALUE | BMI | TUBE VOLTAGE (kV) | TUBE CURRENT (mA) | PULSE TIME (msec) |
| ANALYSIS 1 (ABSENCE OF DYNAMIC NALYSIS) OR (FE-mode/BS-mode) | BATHYPNEA | STANDING POSITION | 180 | 6 | 15 | 6000 | 10– | 100 | 32 | 1 |
| | | | | | | | 20– | 100 | 32 | 3 |
| | | | | | | | 30– | 100 | 32 | 5 |
| | | | | | | | 40– | 100 | 32 | 7 |
| ANALYSIS 2 (PL-mode/DM-mode) | BATHYPNEA | STANDING POSITION | 180 | 10 | 15 | 4500 | 10– | 100 | 32 | 1 |
| | | | | | | | 20– | 100 | 32 | 4 |
| | | | | | | | 30– | 100 | 32 | 7 |
| | | | | | | | 40– | 100 | 32 | 10 |
| ANALYSIS 3 (PH-mode) | BREATH HOLD | DECUBITUS POSITION | 120 | 15 | 7 | 3000 | 10– | 100 | 32 | 1 |
| | | | | | | | 20– | 100 | 32 | 3 |
| | | | | | | | 30– | 100 | 32 | 5 |
| | | | | | | | 40– | 100 | 32 | 7 |

| FIRST ORDER INFORMATION | | RADIOGRAPHING CONDITION A | | | | TARGET IMAGE QUALITY | SECOND ORDER INFORMATION | RADIOGRAPHING CONDITION B | | | |
|---|---|---|---|---|---|---|---|---|---|---|---|
| DYNAMIC ANALYSIS ITEM / PRESENCE OR ABSENCE OF DYNAMIC ANALYSIS | RESPIRATION PROTOCOL | RADIOGRAPHING POSTURE | SID (cm) | FRAME RATE (FPS) | RADIOGRAPHING TIME (sec) | TARGET S-VALUE | BMI | TUBE VOLTAGE (kV) | TUBE CURRENT (mA) | PULSE TIME (msec) | DOSE ($\mu$ Gy/1f) |
| ANALYSIS 1 (ABSENCE OF DYNAMIC NALYSIS) (FE-mode/BS-mode) | BATHYPNEA | STANDING POSITION | 180 | 6 | 15 | 6000 | 10– | 100 | 32 | 1 | 1 |
| | | | | | | | 20– | 100 | 32 | 3 | 3 |
| | | | | | | | 30– | 100 | 32 | 5 | 5 |
| | | | | | | | 40– | 100 | 32 | 7 | 7 |
| ANALYSIS 2 (PL-mode/DM-mode) | BATHYPNEA | STANDING POSITION | 180 | 10 | 15 | 4500 | 10– | 100 | 32 | 1 | 1 |
| | | | | | | | 20– | 100 | 32 | 4 | 4 |
| | | | | | | | 30– | 100 | 32 | 7 | 7 |
| | | | | | | | 40– | 100 | 32 | 10 | 10 |
| ANALYSIS 3 (PH-mode) | BREATH HOLD | DECUBITUS POSITION | 120 | 15 | 7 | 3000 | 10– | 100 | 32 | 1 | 3 |
| | | | | | | | 20– | 100 | 32 | 3 | 5 |
| | | | | | | | 30– | 100 | 32 | 5 | 13 |
| | | | | | | | 40– | 100 | 32 | 7 | 18 |

RADIOGRAPHING CONTROL APPARATUS, RECORDING MEDIUM, AND RADIOGRAPHING SYSTEM

CROSS-REFERENCE TO RELATED APPLICATIONS

The entire disclosure of Japanese Patent Application No. 2022-007601 filed on Jan. 21, 2022 is incorporated herein by reference in its entirety.

TECHNICAL FIELD

The present invention relates to a radiographing control apparatus, a recording medium, and a radiographing system.

DESCRIPTION OF THE RELATED ART

In recent years, serial imaging (dynamic radiographing) in a significantly short time by radiographing has made it possible to obtain an image (called a dynamic image) including a captured motion of a target site in a living body (a site to be tested or diagnosed).

For taking a dynamic image suitable for diagnosis or analysis, radiographing conditions, such as a tube voltage of a radiation source and a tube current-time product, are required to be appropriately set.

In this respect, according to JP 2010-172362A, an image feature quantity having a correlation with the radiographing condition of a radiograph input from the radiographic imaging apparatus is adjusted. A radiograph processing apparatus that corrects the radiographing condition for next radiographing in accordance with adjustment of the image feature quantity is described in JP 2010-172362A.

JP 2021-112471A describes a radiographing condition output apparatus that inputs object information into a learned model for outputting the radiographing condition of a cone-beam CT image used to align the position of an object, and outputs the radiographing condition.

JP 5195907B described a dynamic radiographing control apparatus that determines a frame rate used for dynamic radiographing, based on an upper limit frame rate at which an indicator value indicating the image quality of a frame image initially obtained by dynamic radiographing is equal to or lower than a predetermined reference value, and a lower limit frame rate that is the minimum required to diagnose the dynamics of the radiograph site.

SUMMARY OF THE INVENTION

However, the target image quality set in conventional dynamic radiographing is constant irrespective of presence or absence of dynamic analysis executed for a dynamic image and a dynamic analysis item. In this case, there is a problem that with a certain dynamic analysis item, the image quality of an obtained dynamic image is low and the accuracy of analysis is low. There is another problem that with a certain dynamic analysis item, the image quality is excessively high, and the dose to a patient as an object is unnecessarily high.

The problem described above are not solved in JP 2010-172362A, JP 2021-112471A or JP 5195907B.

The present invention has an object to provide a radiographing control apparatus, a recording medium and a radiographing system that can set a radiographing condition more suitable for dynamic radiographing.

To achieve at least one of the abovementioned objects, according to an aspect of the present invention, a radiographing control apparatus reflecting one aspect of the present invention is a radiographing control apparatus emitting radiation to an object and obtaining a plurality of frame images to control dynamic radiographing that radiographs dynamics of the object, the radiographing control apparatus including a hardware processor that:

obtains first order information that includes at least one of information on presence or absence of dynamic analysis executed for a dynamic image obtained by the dynamic radiographing, and information on a dynamic analysis item;

determines a first radiographing condition and a target image quality, based on the obtained first order information; and determines a second radiographing condition for achieving the determined target image quality.

To achieve at least one of the abovementioned objects, according to an aspect of the present invention, a recording medium reflecting one aspect of the present invention is a non-transitory computer readable recording medium storing a program causing a computer of a radiographing control apparatus emitting radiation to an object and obtaining a plurality of frame images to control dynamic radiographing that radiographs dynamics of the object to perform:

obtaining first order information that includes at least one of information on presence or absence of dynamic analysis executed for a dynamic image obtained by the dynamic radiographing, and information on a dynamic analysis item;

determining a first radiographing condition and a target image quality, based on the obtained first order information; and determining a second radiographing condition for achieving the determined target image quality.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein.

DETAILED DESCRIPTION

Hereinafter, referring to FIGS. 1 to 8, an embodiment of a radiographing control apparatus, a recording medium, and a radiographing system according to the present invention is described.

Note that various limitations technologically preferable to implement the present invention are applied to the embodiment described below, but do not limit the technological scope of the present invention to the following embodiment and illustrated examples.

Figure 1:
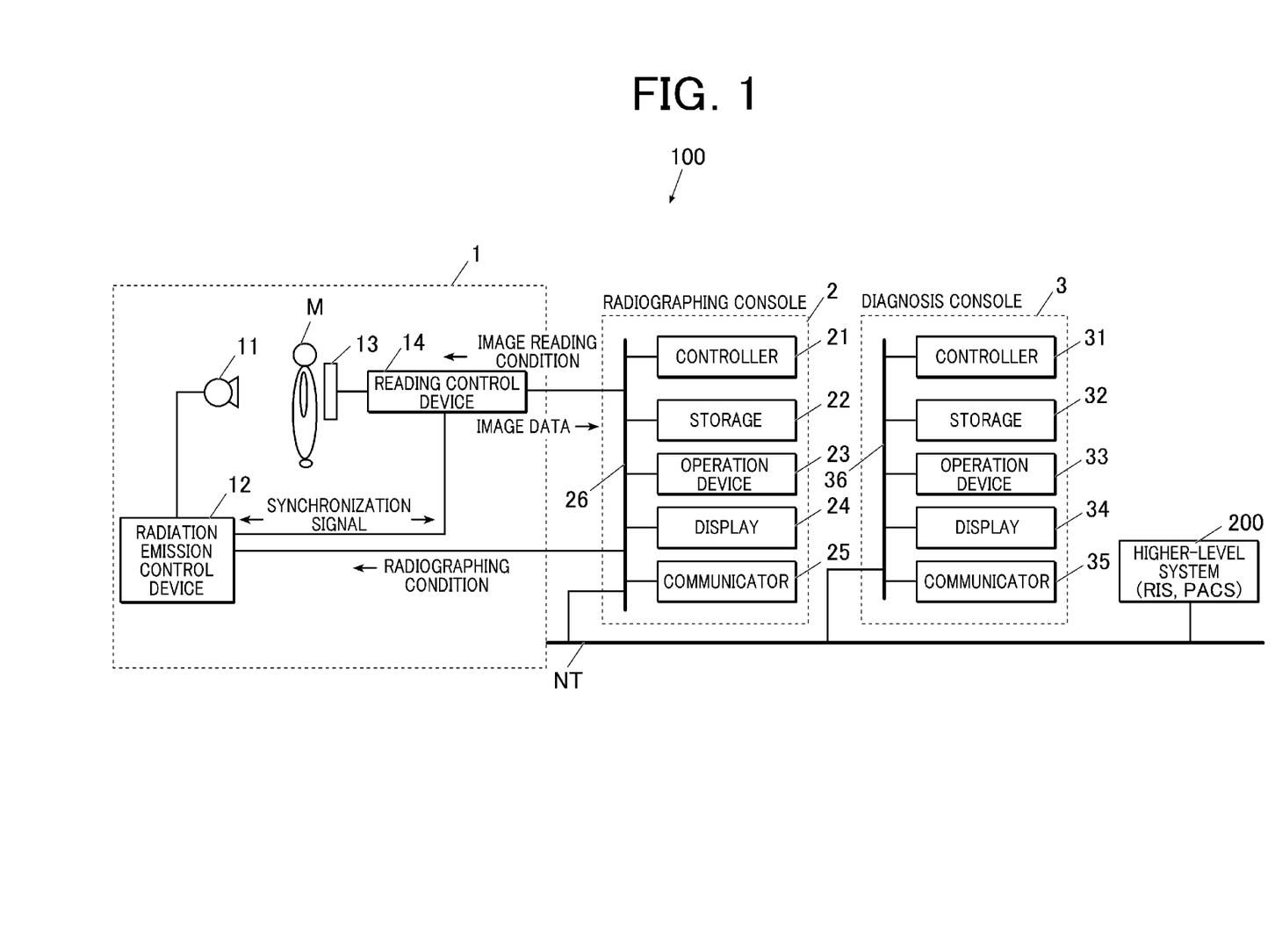
FIG. 1 is a main configuration diagram showing a system configuration of a radiographing system according to this embodiment.

FIG. 1 shows an overall configuration of a radiographing system 100 according to this embodiment.

As shown in FIG. 1, the radiographing system 100 has a configuration where a radiographing apparatus 1, and a radiographing console 2, which is a radiographing control apparatus, are connected to each other by a communication cable and the like, and the radiographing console 2 and a diagnosis console 3 are connected to each other via a communication network NT, such as a LAN (Local Area Network). Each of apparatuses constituting the radiographing system 100 conforms to DICOM (Digital Image and Communications in Medicine) standards, and communication among the apparatuses is performed in conformity with DICOM.

The radiographing system 100 is connected to a higher-level system 200 (e.g., a radiology information system (RIS), a picture archiving and communication system (PACS), etc.) via the communication network NT.

The higher-level system 200 transmits radiographing order information where information required for radiographing is set, to the radiographing console 2 via the communication network NT. The radiographing order information includes first order information (described later) and second order information (described later). The radiographing system 100 may include a radiographing stage (for standing position radiographing, for decubitus position radiographing, for longitudinal radiographing, etc.), not shown, for holding a radiation detector 13 (described later).

The radiographing system 100 may be installed in a radiographing room, or be a visiting car (configured to allow the radiographing apparatus 1 to be moved).

[Configuration of Radiographing Apparatus 1]

The radiographing apparatus 1 is, for example, radiographing equipment that radiographs the dynamics of a living body, such as morphological changes of expansion and contraction of lungs due to respiratory movement, heartbeats and the like.

As shown in FIG. 1, the radiographing apparatus 1 includes a radiation source 11, a radiation emission control device 12, a radiation detector 13, and a reading control device 14.

Here, dynamic radiographing is what obtains images by radiographing an object including a target site (e.g., the lung field and therearound in the chest, a heart, etc.) in a living body, i.e., what obtains a plurality of images by irradiating the object with pulsed radiation, such as X-rays, repeatedly at predetermined time intervals (pulse irradiation) or with seamless and continuous radiation having a low dose rate (continuous irradiation). A series of images obtained by the dynamic radiographing is called a dynamic image. In the dynamic image, data through one time of radiographing includes a plurality of images, and the images constituting the dynamic image are called frame images.

Note that in the following embodiment, a case of dynamic radiographing by pulse irradiation is exemplified and description is made. Target sites to be subjected to dynamic radiographing include the lung field and therearound in the chest (the lung field and the diaphragm), the heart, pulmonary vessels, intercostal muscle, thorax, etc., the intestines, esophagus and the like in the gastric region, etc., various orthopedic sites, such as the knees, elbows, neck, and spine, and various tissues.

The radiation source 11 is disposed at a position facing the radiation detector 13 with an object M being allowed to intervene, and irradiates the object M with radiation (X-rays) according to control by the radiation emission control device 12.

The radiation emission control device 12 is connected to the radiographing console 2, and controls the radiation source 11 based on radiographing conditions input from the radiographing console 2, and performs radiographing. The radiographing conditions input from the radiographing console 2 include, for example, radiographing modes (still image radiographing, and dynamic image radiographing), the radiographing posture, the distance between the radiation source 11 and the radiation detector 13 (SID), the pulse rate, the radiographing time that is a time required for one time of radiographing, the pulse width (pulse time), the pulse interval, the number of frames per one time of radiographing, the tube current value, the tube voltage value, and the applied filter type. The pulse rate is the number of radiation emission times per second, and coincides with the frame rate described later. The pulse width is the radiation emission time per radiation emission. The pulse interval is a time from the start of a radiation emission to the start of the next radiation emission, and coincides with the frame interval described later.

The radiation detector 13 is made up of a semiconductor image sensor, such as an FPD (Flat Panel Detector). The FPD includes, for example, a glass substrate. A plurality of detection elements (pixels) that detect radiation having been emitted from the radiation source 11 and passed through at least the object M, depending on the intensity, convert the detected radiation into an electric signal and accumulate the signal, are arranged in a matrix manner at predetermined positions on the substrate. Each pixel includes a switcher, such as TFT (Thin Film Transistor), for example. FPDs include an indirection conversion type that converts X-rays into an electric signal through a scintillator by a photoelectric conversion element, and a direct conversion type that directly converts X-rays into an electric signal. Any of the types may be adopted.

The radiation detector 13 is provided so as to face the radiation source 11 with the object M being allowed to intervene.

The reading control device 14 is connected to the radiographing console 2. The reading control device 14 controls the switcher of each pixel of the radiation detector 13, based on image reading conditions input from the radiographing console 2, switches reading of the electric signal accumulated in the corresponding pixel, and reads the electric signal accumulated in the radiation detector 13, thus obtaining image data. The image data is a frame image. The reading control device 14 outputs the obtained frame image to the radiographing console 2. The image reading conditions include, for example, the frame rate, the frame interval, the pixel size, and the image size (matrix size). The frame rate is the number of frame images obtained per second, and coincides with the pulse rate. The frame interval is a time from the start of one operation of obtaining the frame image to the start of the operation of obtaining the next frame image, and coincides with the pulse interval.

Here, the radiation emission control device 12 and the reading control device 14 are connected to each other, and mutually exchange a synchronization signal and synchronize a radiation emission operation with an image reading operation.

[Configuration of Radiographing Console 2]

The radiographing console 2 outputs the radiographing conditions and the image reading conditions to the radiographing apparatus 1 and controls radiographing by the radiographing apparatus 1, and the operation of reading radiographs, while displaying the dynamic image obtained by the radiographing apparatus 1, for verifying positioning by a radiographing operator, such as a radiation technologist, and verifying whether the image is an image suitable for diagnosis.

As shown in FIG. 1, the radiographing console 2 includes a controller 21 (hardware processor), a storage 22, an operation device 23, a display 24, and a communicator 25. The components are connected to each other by a bus 26.

The controller 21 includes a central processing unit (CPU) and a random access memory (RAM). In accordance with the operation of the operation device 23, the CPU of the controller 21 reads a system program and various processing programs stored in the storage 22, deploys the programs in the RAM, and executes various processes including a radiographing condition determination process described later in accordance with the deployed programs, and integrally controls the operations of the components of the radiographing console 2, the radiation emission operation and the reading operation of the radiographing apparatus 1.

The controller 21 obtains first order information that includes at least one of information on presence or absence of dynamic analysis executed for a dynamic image obtained by the dynamic radiographing, and information on a dynamic analysis item. Here, the controller 21 functions as a first obtainer.

The controller 21 determines a first radiographing condition and a target image quality, based on the first order information obtained by the first obtainer. Here, the controller 21 functions as a first determiner.

The controller 21 determines a second radiographing condition for achieving the target image quality determined by the first determiner. Here, the controller 21 functions as a second determiner.

The controller 21 obtains second order information that is information about a radiograph site. Here, the controller 21 functions as a second obtainer.

The storage 22 includes a nonvolatile semiconductor memory, and a hard disk and the like. The storage 22 stores the various programs executed by the controller 21, parameters required to execute processes by the programs, or data on a processing result and the like. For example, the storage 22 stores a program to execute the radiographing condition determination process shown in FIG. 4.

The various programs are stored in a form of readable program code. The controller 21 sequentially executes the operation in accordance with the program code.

The storage 22 stores a radiographing condition table (described later) that includes a first table and a second table.

The operation device 23, which includes a keyboard including cursor keys, numerical input keys, various kinds of function keys, and a pointing device such as a mouse, outputs an instruction signal input through key operation on the keyboard and mouse operation, to the controller 21. The operation device 23 may include a touch panel on a display screen of the display 24. In this case, the instruction signal input through the touch panel is output to the controller 21.

The display 24 includes a monitor, such as an LCD (Liquid Crystal Display) or a CRT (Cathode Ray Tube), and displays an input instruction from the operation device 23, data and the like in accordance with the instruction of a display signal input from the controller 21.

The communicator 25 includes a LAN adaptor, a modem, a TA (Terminal Adapter) or the like, and controls data transmission and reception between apparatuses connected to the communication network NT.

[Description of Radiographing Condition Table]

Next, the radiographing condition table stored in the storage 22 is described.

Figure 2:
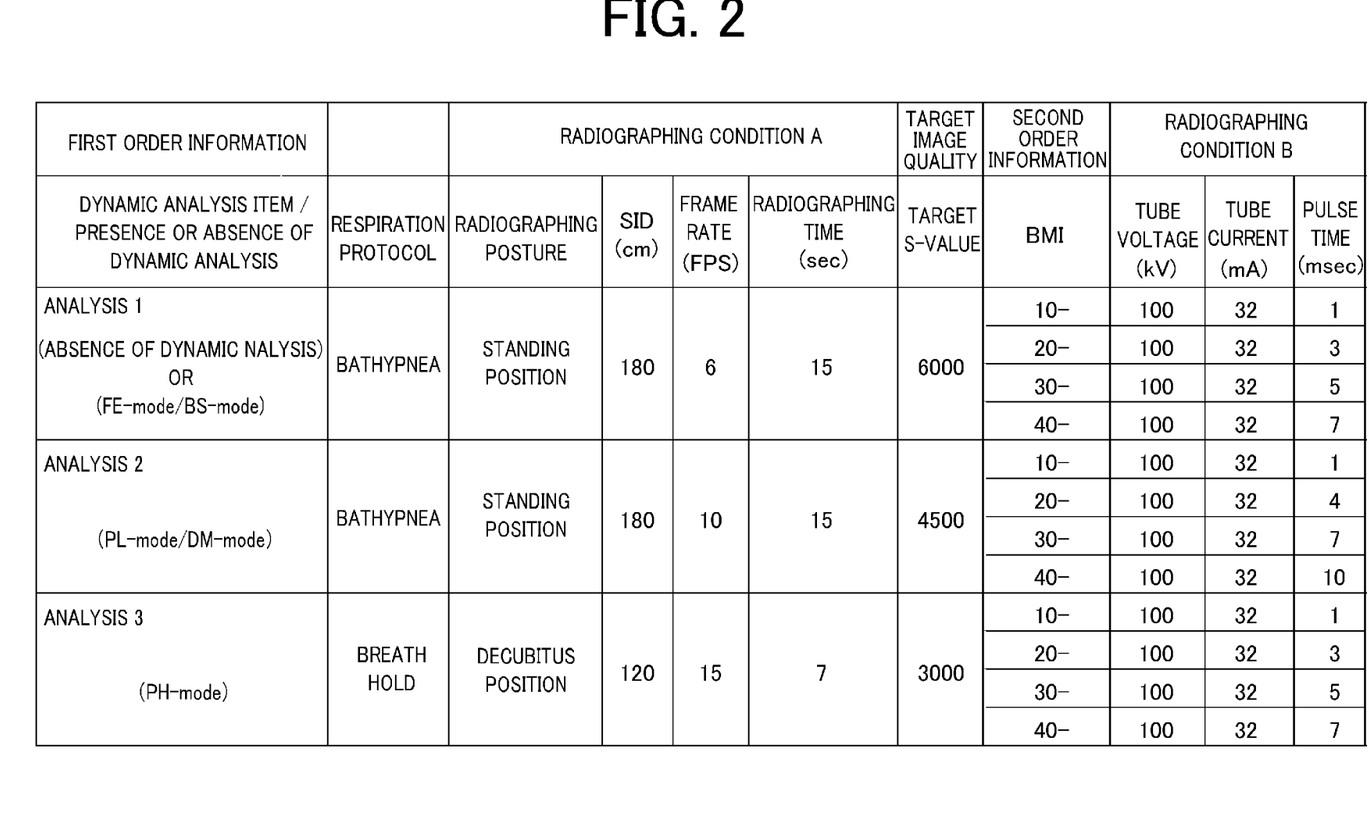
FIG. 2 shows an example of a radiographing condition table.

FIG. 2 shows an example of the radiographing condition table.

The radiographing condition table adopts the dynamic analysis item or the presence or absence of dynamic analysis that is the first order information, as the major category, and provides a respiration protocol (instruction information about respiration of an object (patient) during dynamic radiographing), a radiographing condition A that is first radiographing condition (the radiographing posture, SID, frame rate, and radiographing time), and the target image quality. That is, the radiographing condition table (first table) indicates the relationship between the first order information and the first radiographing condition.

The target image quality is a target signal value in the region of interest (ROI) of dynamic analysis executed for the dynamic image obtained by dynamic radiographing, or a target value of an indicator indicating the image quality, and is a minimum value required to execute dynamic analysis accurately.

In the example of the radiographing condition table shown in FIG. 2, "ANALYSIS 1," "ANALYSIS 2" and "ANALYSIS 3" are major categories. Specifically, "ANALYSIS 1" indicates a case of absence of dynamic analysis, or a case where the dynamic analysis item is "FE-mode: frequency enhancement process" or "BS-mode: bone suppression process." "ANALYSIS 2" indicates a case where the dynamic analysis item is "PL-mode: a process of extracting signal value variation accompanied by respiration, or "DM-mode: a process of tracking a specific component in the amount of diaphragm variation." "ANALYSIS 3" indicates a case where the dynamic analysis item is "PH-mode: a process of extracting signal value variation accompanied by vascular pulsation."

Note that the dynamic analysis items are not limited to the items described above, and may be other items.

Figure 3A:
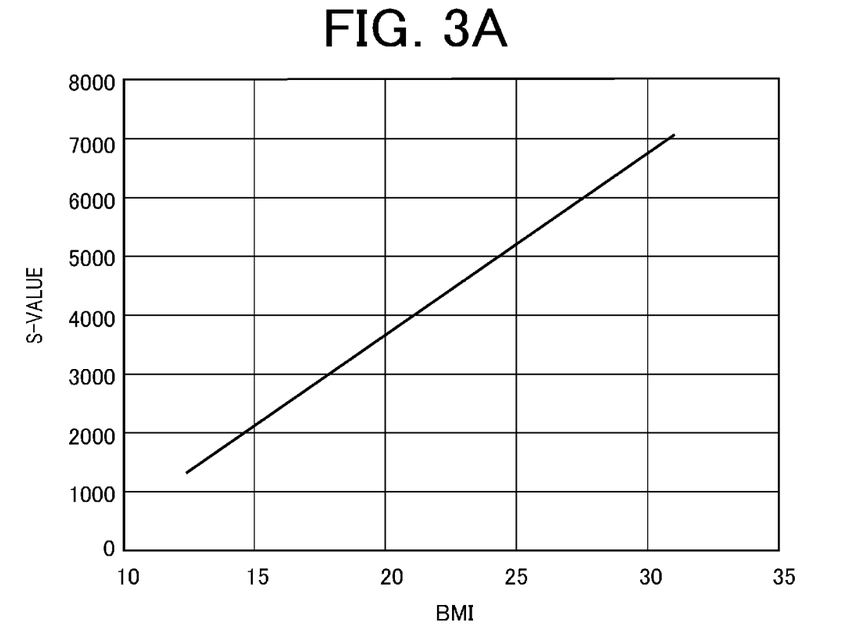
FIG. 3A shows a relationship between the S-value and the BMI of a patient as an object.

Here, FIG. 3A shows the relationship between the S-value that is an indicator indicating the image quality, and the BMI of a patient serving as an object.

The S-value is a value corresponding to the density of an output image obtained as a result of a normalization process when the object is radiographed in freely selected radiographing conditions. The value also corresponds to the sensitivity of film required when the reference signal value set in ROI is intended to be finished to have densities indicated by densities DL (density in a low density area) and DH (density in a high density area). The S-value has a relationship inversely proportional to the reference signal value. The reference signal value has a relationship proportional to the dose. Accordingly, the S-value is inversely proportional to the dose. Consequently, a lower S-value indicates a higher image quality, and a higher S-value indicates a lower image quality.

Any of conventionally known technologies (e.g., technologies described in JP 2018-149166A, JP 2010-188041A and the like) can be used to calculate the S-value.

Note that in this embodiment, instead of the S-value, the EI (Exposure Index) value, which is an industry standard dose index value, may be used. Alternatively, a signal value proportional to the dose with which the radiation detector 13 is irradiated may be used as it is.

The S-value that is an indicator indicating the image quality (sometimes called a sensitivity indicator) has a definition and a name that vary depending on each manufacturer (each radiographing system). However, application is similarly made even to any of the other different indicators.

The S-value and the BMI of the patient has a correlation indicated by linear approximation or exponential approximation (FIG. 3A shows the case of linear approximation). Consequently, as shown in FIG. 2, the BMI can be used to classify the radiographing condition.

That is, the radiographing condition table adopts the numerical value of the BMI (Body Mass Index) of the patient that is second order information, as the minor category, and provides a radiographing condition B (the tube voltage value, tube current value, and pulse time) that is second order information based on the target image quality. That is, the radiographing condition table (second table) indicates the relationship between the target image quality and the second order information, and the second radiographing condition.

In the example shown in FIG. 2, as the minor categories, the BMI is classified into 10 or higher and less than 20, 20 or higher and less than 30, 30 or higher and less than 40, and 40 or higher.

Figure 3B:
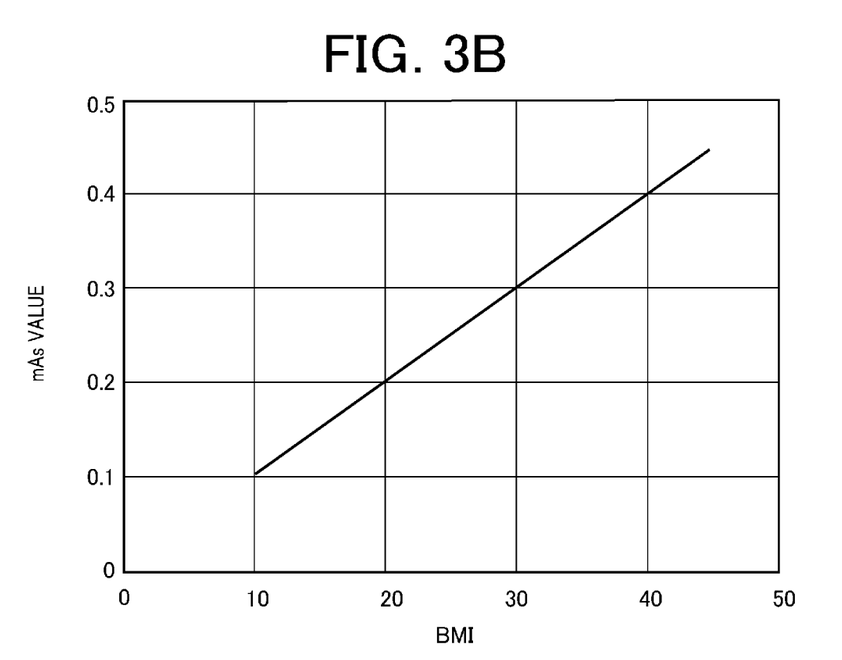
FIG. 3B shows a relationship between the mAs value and the BMI of the patient as the object.

FIG. 3B shows the relationship between the mAs value (tube current-time product) and the BMI of the patient serving as the object, for obtaining the target S-value (or the target signal value) for achieving the target image quality. The mAs value is the product of the tube current value (mA) and the irradiation time (sec).

The mAs value and the BMI of the patient have a correlation indicated by linear approximation or exponential approximation (FIG. 3B shows the case of linear approximation). Consequently, as shown in FIG. 2, in a case where the tube current value is made constant, the pulse time is provided so that the higher the BMI of the patient is, the longer the pulse time is (as a result, the mAs value becomes large).

Note that in the radiographing condition table, the first order information may be the respiration protocol, and the respiration protocol may be adopted as the major category. In this case, the radiographing condition table (first table) provides the dynamic analysis item (or presence or absence of dynamic analysis), the radiographing condition A, and the target image quality.

[Configuration of Diagnosis Console 3]

The diagnosis console 3 obtains the dynamic image from the radiographing console 2, analyzes the obtained dynamic image, generates an image and various data items, as an analysis result, and displays the generated analysis result, thus providing information for supporting diagnosis by a doctor.

As illustrated in FIG. 1, the diagnosis console 3 includes a controller 31, a storage 32, an operation device 33, a display 34, and a communicator 35, which are connected by a bus 36.

The controller 31 includes a CPU, and a RAM. In accordance with the operation of the operation device 33, the CPU of the controller 31 reads a system program and various processing programs stored in the storage 32, deploys the programs in the RAM, and executes various processes in accordance with the deployed programs, and integrally controls the operations of the components of the diagnosis console 3.

The storage 32 includes a nonvolatile semiconductor memory, and a hard disk. The storage 32 stores the various programs including programs for allowing the controller 31 to execute an image analysis process, a dynamic analysis process and the like, parameters required to execute the processes by the programs, or data on a processing result and the like. These various programs are stored in a form of readable program code. The controller 31 sequentially executes the operation in accordance with the program code.

The operation device 33, which includes a keyboard including cursor keys, numerical input keys, various kinds of function keys, and a pointing device such as a mouse, outputs an instruction signal input through key operation on the keyboard and mouse operation, to the controller 31. The operation device 33 may include a touch panel on a display screen of the display 34. In this case, the instruction signal input through the touch panel is output to the controller 31.

The display 34 is made up of a monitor, such as an LCD or a CRT, and performs various types of displaying in accordance with the instruction of the display signal input from the controller 31.

The communicator 35 includes a LAN adaptor, a modem, a TA or the like, and controls data transmission and reception between apparatuses connected to the communication network NT.

[Operation of Radiographing Console 2]

Next, the operation of the radiographing console 2 as the aforementioned radiographing control apparatus is described.

Figure 4:
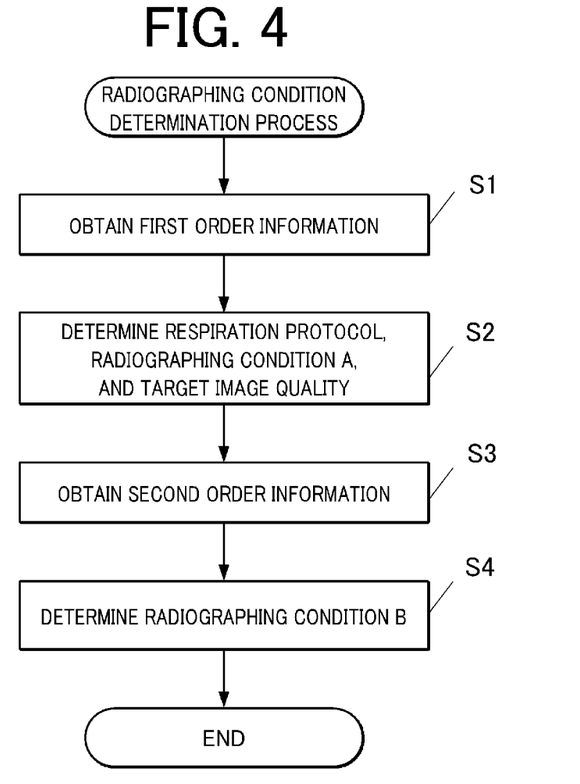
FIG. 4 is a flowchart showing the flow of a radiographing condition determination process.

The controller 21 of the radiographing console 2 is triggered by the fact that a predetermined condition is satisfied (the radiographing order information is received from the higher-level system 200 or the like), and executes the radiographing condition determination process shown in FIG. 4.

The radiographing order information includes the type of still image radiographing or moving image radiographing, presence or absence of dynamic analysis executed for the radiographed image, dynamic analysis item, patient information on the patient serving as the object (the name, age, height, weight and BMI of the patient), the radiograph site (chest front/side), and the radiographing direction.

In the radiographing condition determination process, first, the controller 21 obtains presence or absence of dynamic analysis or the dynamic analysis item, which is the first order information, from the received first order information (Step S1).

Next, the controller 21 refers to the radiographing condition table, and determines the respiration protocol, the radiographing condition A (first radiographing condition), and the target image quality, based on the presence or absence of dynamic analysis or the dynamic analysis item obtained in Step S1 (Step S2).

Specifically, when the dynamic analysis item obtained in Step S1 is "PL-mode," in the example shown in FIG. 2, the respiration protocol is "BATHYPNEA," the radiographing posture that is the radiographing condition A is "STANDING POSITION," SID is 180 [cm], the frame rate is 10 [FPS], the radiographing time is 15 [sec], and the target image quality (here, for example, the target S-value) is 4500.

Next, the controller 21 obtains the BMI of the patient as the second order information, from the received radiographing order information (Step S3).

Note that in Step S3, the controller 21 may obtain the height and weight of the patient from the radiographing order information, and calculate the BMI from the height and weight.

Next, the controller 21 refers to the radiographing condition table, determines the radiographing condition B (second radiographing condition) based on the target image quality determined in Step S2 and on the BMI of the patient obtained in Step S3 (Step S4), and the processing is finished.

Specifically, when the target image quality determined in Step S2 is 4500 and the BMI of the patient obtained in Step S3 is 20, in the example shown in FIG. 2, for the radiographing condition B, the tube voltage value is 100 [kV], the tube current value is 32 [mA], and the pulse time is 4 [msec].

The controller 21 outputs the radiographing condition A determined in Step S2 and the radiographing condition B determined in Step S4, as the radiographing conditions of the dynamic radiographing, to the radiographing apparatus 1.

(Modification)

Next, a modification of the above embodiment is described.

Hereinafter, the difference from the above embodiment is mainly described. The configuration of the radiographing system 100 in this modification is the same as that of the radiographing system 100 in the embodiment described above.

In this modification, the controller 21 calculates a total dose during the dynamic radiographing, based on the first radiographing condition determined by the first determiner, and the second radiographing condition determined by the second determiner. Here, the controller 21 functions as a calculator.

The controller 21 verifies whether the total dose calculated by the calculator is higher than a predetermined value. Here, the controller 21 functions as a verifier.

Here, the controller 21 issues an alert if the total dose is verified to be higher than the predetermined value by the verifier. Here, the controller 21 functions as a notification controller.

The controller 21 causes a display to display a proposal for reducing a frame rate during the dynamic radiographing or reducing a radiographing time of the dynamic radiographing, if the total dose is verified to be higher than the predetermined value by the verifier. Here, the controller 21 functions as a display controller.

Figure 5:
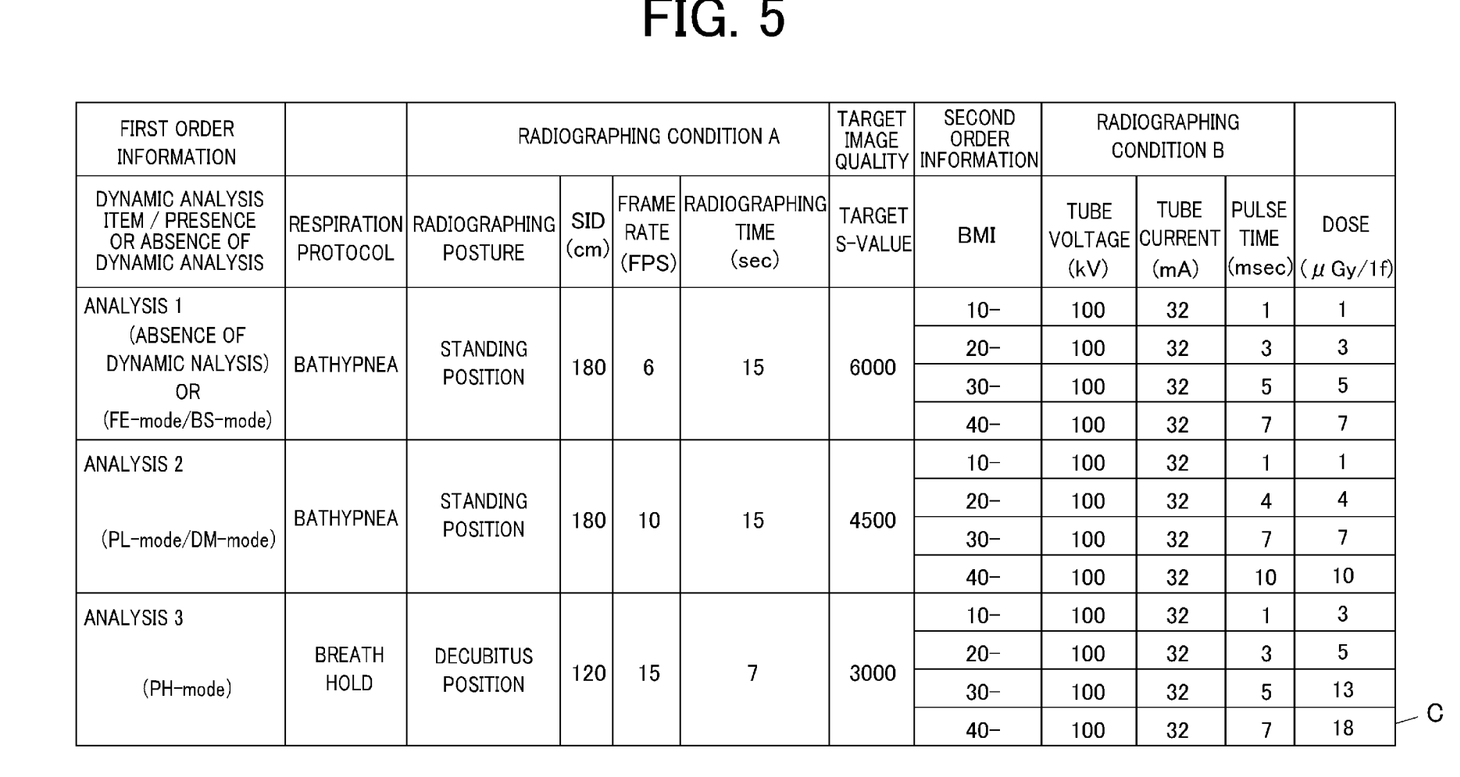
FIG. 5 shows an example of a radiographing condition table in a modification.

FIG. 5 shows an example of a radiographing condition table in this modification.

Similar to the radiographing condition table in the embodiment described above, the radiographing condition table in this modification adopts the dynamic analysis item or the presence or absence of dynamic analysis that is the first order information and is included in the radiographing order information, as the major category, and provides the respiration protocol, the radiographing condition A, and the target image quality. The table adopts the BMI of the patient that is the second order information as the minor category, and provides the radiographing condition B based on the target image quality.

Furthermore, the radiographing condition table in this modification provides the dose in each frame image based on the radiographing condition B.

Figure 6:
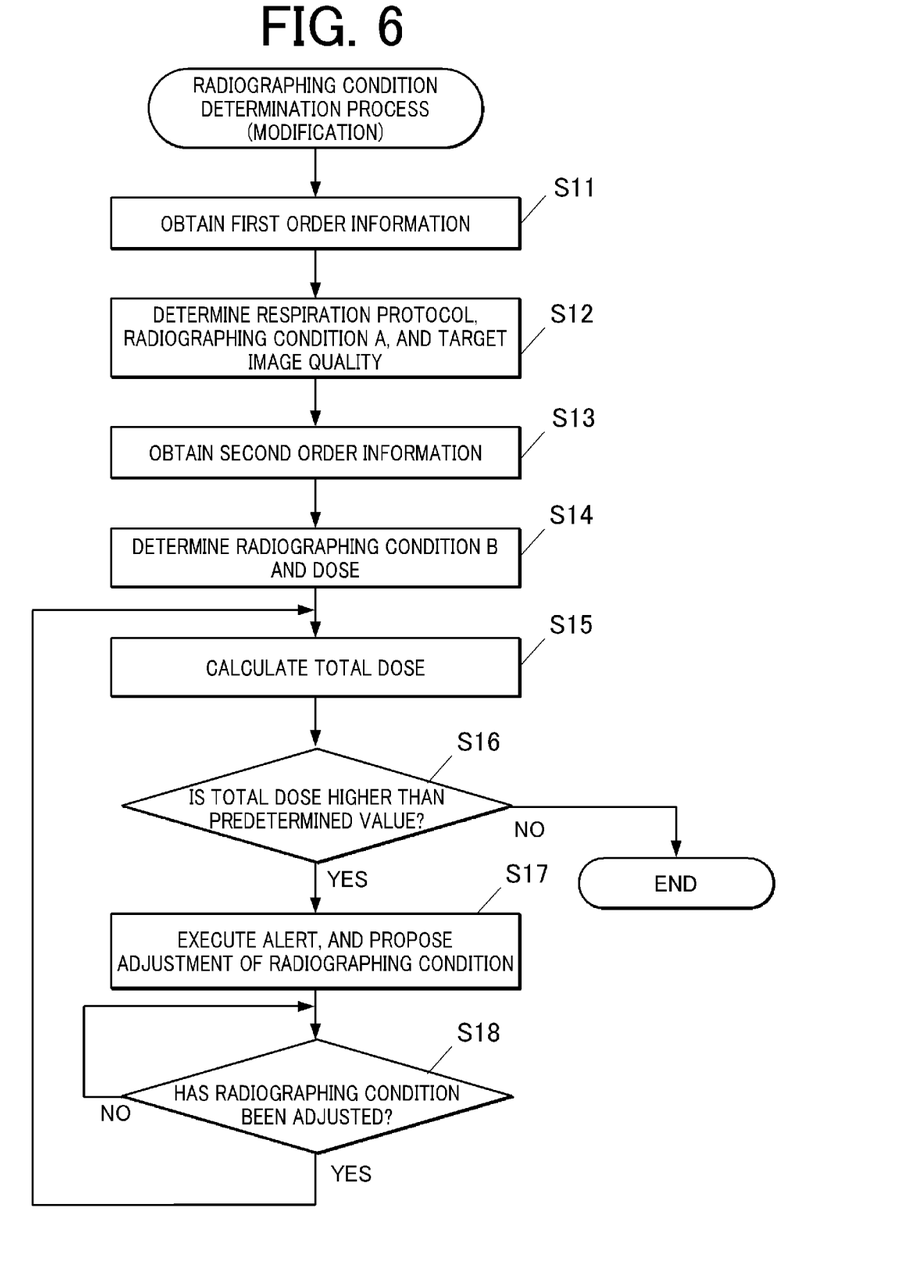
FIG. 6 is a flowchart showing the flow of a radiographing condition determination process in the modification.

In this modification, the controller 21 of the radiographing console 2 is triggered by the fact that a predetermined condition is satisfied (the radiographing order information is received from the higher-level system 200 or the like), and executes the radiographing condition determination process in the modification shown in FIG. 6.

In the radiographing condition determination process in this modification, the controller 21 executes Steps S11 to S13 similar to Steps S1 to S3 in the radiographing condition determination process in the embodiment described above.

Next, the controller 21 refers to the radiographing condition table, determines the radiographing condition B (second radiographing condition) and the dose in each frame image, based on the target image quality determined in Step S12 and on the BMI of the patient obtained in Step S13 (Step S14).

For example, when the target image quality determined in Step S12 is 3000 and the BMI of the patient obtained in Step S13 is 40 (in the case of condition C shown in FIG. 5), in the example shown in FIG. 5, for the radiographing condition B, the tube voltage value is 100 [kV], the tube current value is 32 [mA], the pulse time is 7 [msec], and the dose in each frame is 18 [μGy/1 f].

Next, the controller 21 calculates the total dose that is the dose in a single time of dynamic radiographing, based on the radiographing condition A determined in Step S12 and the dose in each frame image determined in Step S14 (Step S15).

For example, in the case of the condition C shown in FIG. 5, for the radiographing condition A, the frame rate is 15 [FPS], the radiographing time is 7 [sec], and the dose in each frame image is 18 [μGy/1 f]. In this case, the total dose is 18 [μGy/1 f]×15 [FPS]×7 [sec]=1890 [μGy].

Next, the controller 21 verifies whether the total dose calculated in Step S15 is higher than the predetermined value or not (Step S16).

The predetermined value is a value less affecting the human body (e.g., 1500 [μGy]), and may be freely set through the operation device 23 or the communicator 25.

If the total dose is less than the predetermined value (Step S16: NO), the controller 21 finishes this processing. The controller 21 outputs the radiographing condition A determined in Step S12 and the radiographing condition B determined in Step S14, as the radiographing conditions of the dynamic radiographing, to the radiographing apparatus 1.

If the total dose is higher than the predetermined value (Step S16: Yes), the controller 21 displays that the total dose is higher than the predetermined value, as an alert, on the display 24. While issuing the alert, the controller 21 displays a proposal of reducing the frame rate or the radiographing time, which is the radiographing condition A, on the display 24 (Step S17).

Next, in accordance with an input operation of the user through the operation device 23, the controller 21 verifies whether the frame rate or the radiographing time, which is the radiographing condition A, has been adjusted (Step S18).

If the frame rate or the radiographing time has not been adjusted (Step S18: NO), the controller 21 returns the processing to Step S18. That is, adjustment of the frame rate or the radiographing time is waited for by the user.

If the frame rate or the radiographing time has been adjusted (Step S18: YES), the controller 21 proceeds the processing to Step S15.

In Step S15, the controller 21 calculates the total dose, based on the value adjusted in Step S18.

For example, if the frame rate is changed to 10 [FPS] from the condition C shown in FIG. 5 by the user in Step S18, the total dose is 18 [μGy/1 f]×10 [FPS]×7 [sec]=1260 [μGy].

If the total dose calculated based on the value adjusted in Step S18 is lower than the predetermined value (Step S16:

NO), the controller 21 finishes this processing. The controller 21 outputs the frame rate or the radiographing time adjusted in Step S18, the radiographing condition A except the frame rate or the radiographing time determined in Step S12 and adjusted in Step S18, and the radiographing condition B determined in Step S14, as radiographing conditions of dynamic radiographing, to the radiographing apparatus 1.

As described above, by adjusting the frame rate or the radiographing time so that the total dose is not higher than the predetermined value, the safe radiographing conditions of dynamic radiographing less affecting the human body can be determined.

(Test Screen)

Figure 7:
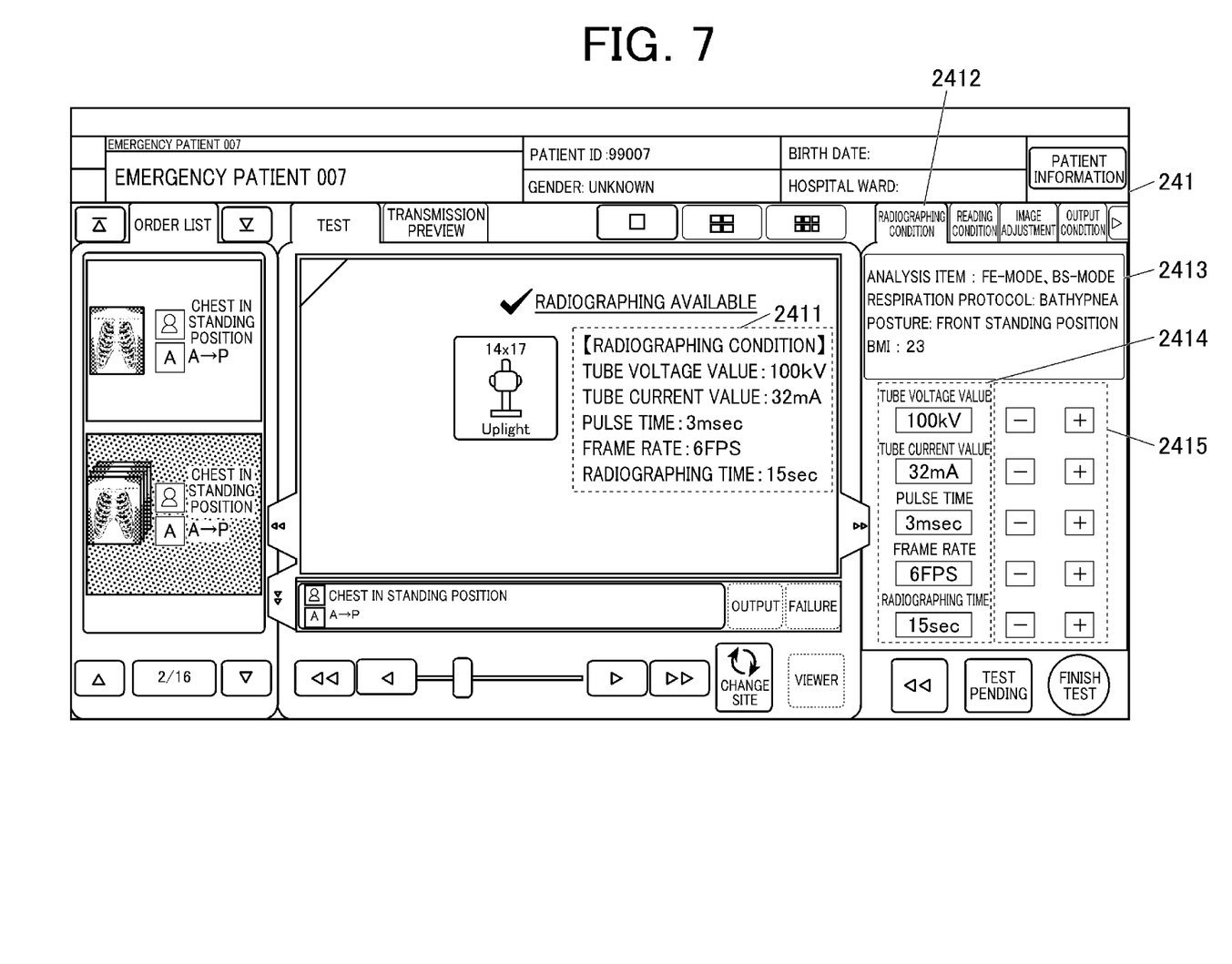
FIG. 7 shows an example of a test screen.

Next, a test screen that the controller 21 displays on the display 24 upon receipt of the radiographing order information from the higher-level system 200 is described.

FIG. 7 shows an example of a test screen 241 displayed on the display 24.

Based on the received radiographing order information, the controller 21 displays the radiographing conditions (the radiographing condition A and the radiographing condition B) determined in the radiographing condition determination process, on a display item 2411 in the test screen 241. In the example shown in FIG. 7, the tube voltage value, the tube current value, the pulse time, the frame rate, and the radiographing time are displayed as radiographing conditions.

In a display item 2413 at a radiographing condition tab 2412 in the test screen 241, the controller 21 displays the dynamic analysis item and the BMI of the patient included in the received radiographing order information. Based on the received radiographing order information, the controller 21 displays, on the display item 2413, the respiration protocol and the radiographing posture determined in the radiographing condition determination process.

Based on the received radiographing order information, the controller 21 displays the radiographing conditions (the radiographing condition A and the radiographing condition B) determined in the radiographing condition determination process, on a display item 2414 at the radiographing condition tab 2412. In the example shown in FIG. 7, the tube voltage value, the tube current value, the pulse time, the frame rate, and the radiographing time are displayed as radiographing conditions.

For example, in the radiographing condition determination process of the above modification, the controller 21 accepts adjustment of the radiographing conditions by an input operation of the user through an adjustment button 2415 at the radiographing condition tab 2412. In the example shown in FIG. 7, by pressing any of "+" buttons or "−" buttons of the adjustment button 2415, the tube voltage value, the tube current value, the pulse time, the frame rate and the radiographing time can be adjusted.

When the controller 21 accepts adjustment of the radiographing condition, the controller 21 displays the adjusted radiographing condition on the display item 2411 and the display item 2414.

Note that in the example shown in FIG. 7, it is configured so that the tube current value and the pulse time are displayed as radiographing conditions on the display item 2414, and can be adjusted through the adjustment button 2415. However, the configuration is not limited thereto. It may be configured so that instead of the tube current value and the pulse time, the mAs value is displayed on the display item 2414, and the mAs value can be adjusted through the adjustment button 2415.

Figure 8:
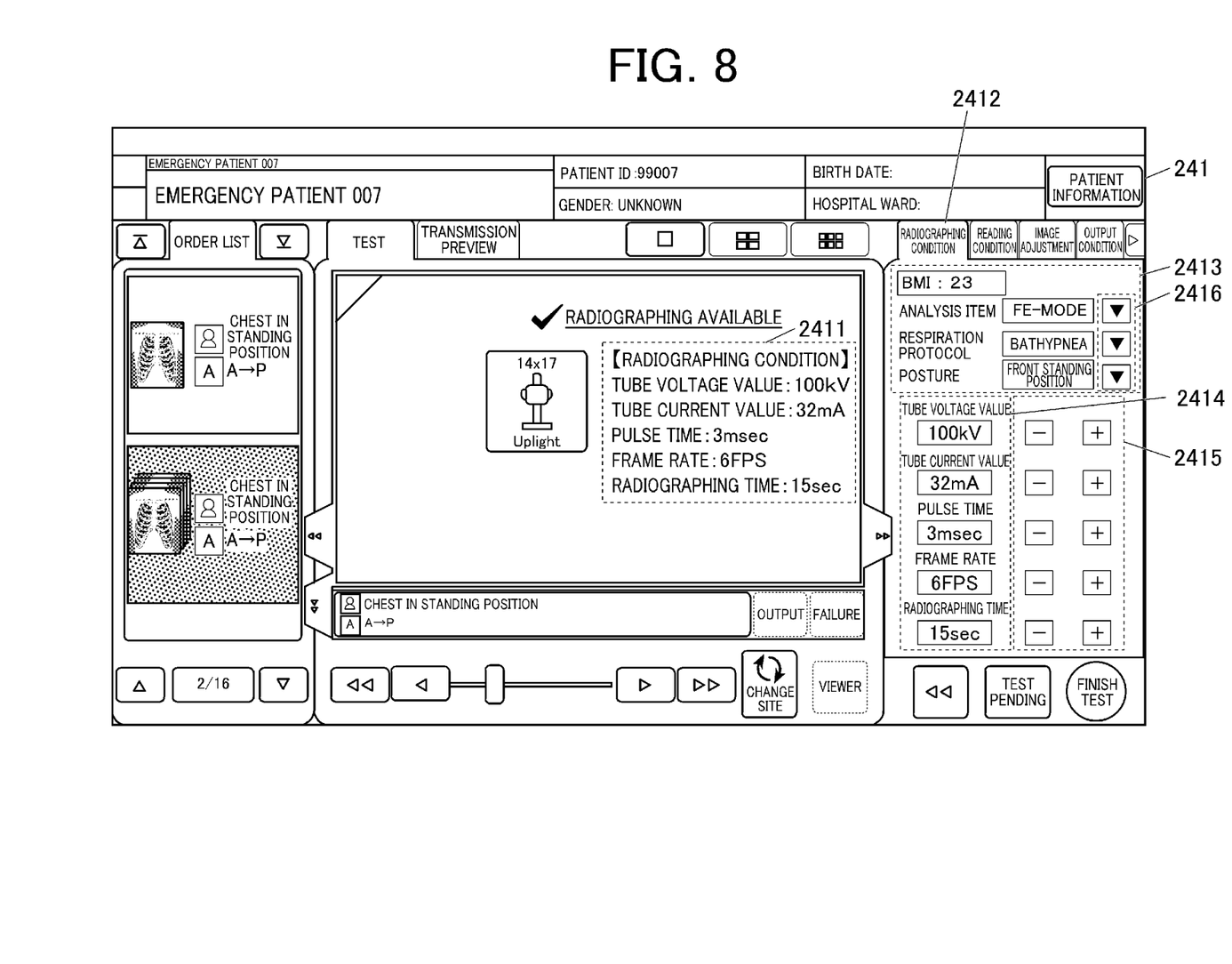
FIG. 8 shows an example of a test screen.

FIG. 8 shows an example of a test screen 241 in a mode different from that in FIG. 7.

Hereinafter, parts different from those in FIG. 7 are mainly described.

In the example shown in FIG. 8, the controller 21 accepts selection of the dynamic analysis item, the respiration protocol and the radiographing posture, by an input operation of the user through a selection button 2416 of the radiographing condition tab 2412.

For example, it is configured so that the dynamic analysis item can be selected from among "FE-MODE," "BS-MODE," "PL-MODE" and "DM-MODE" through the selection button 2416. Note that a plurality of dynamic analysis items may be selected.

For example, it is configured so that the respiration protocol can be selected from among "BATHYPNEA," "QUIET BREATHING" and "BREATH HOLD" through the selection button 2416.

For example, it is configured so that the radiographing posture can be selected from among "FRONT STANDING POSITION", "SIDE STANDING POSITION", "FRONT DECUBITUS POSITION", "SIDE DECUBITUS POSITION", "FRONT SEATED POSITION" and "SIDE SEATED POSITION" through the selection button 2416.

Note that when the combination of the dynamic analysis item and the respiration protocol selected by the input operation of the user is not preferable, the controller 21 may display a warning in the test screen 241.

Upon acceptance of selection of the dynamic analysis item, the respiration protocol and the radiographing posture, the controller 21 displays the selected dynamic analysis item, respiration protocol and radiographing posture on the display item 2413.

As shown in FIGS. 7 and 8, it is configured so that the radiographing conditions can be manually changed or modified by an input operation of the user.

As described above, the radiographing console 2 (radiographing control apparatus) according to this embodiment is a radiographing control apparatus emitting radiation to an object and obtaining a plurality of frame images to control dynamic radiographing that radiographs dynamics of the object, the radiographing control apparatus including: a first obtainer (controller 21) that obtains first order information that includes at least one of information on presence or absence of dynamic analysis executed for a dynamic image obtained by the dynamic radiographing, and information on a dynamic analysis item; a first determiner (controller 21) that determines a first radiographing condition and a target image quality, based on the first order information obtained by the first obtainer; and a second determiner (controller 21) that determines a second radiographing condition for achieving the target image quality determined by the first determiner.

Accordingly, more suitable radiographing conditions in dynamic radiographing can be set based on the information on presence or absence of dynamic analysis and the dynamic analysis item, which are the first order information.

In the radiographing console 2 according to this embodiment, the first order information includes instruction information (respiration protocol) about respiration of an object during dynamic radiographing.

Accordingly, more suitable radiographing conditions in dynamic radiographing can be set based on the respiration protocol, which is the first order information.

In the radiographing console 2 according to this embodiment, the first determiner determines the first radiographing condition, based on the first table that indicates the relationship between the first order information and the first radiographing condition.

Consequently, a more suitable radiographing condition in dynamic radiographing can be easily set based on the first table.

In the radiographing console 2 according to this embodiment, the first radiographing condition includes any of a posture of the object during the dynamic radiographing, the distance between the radiation source and the radiation detector that generates an image in accordance with the radiation emitted from the radiation source, a frame rate during the dynamic radiographing, and radiographing time of the dynamic radiographing.

Consequently, the posture of the object, the distance between the radiation source and the radiation detector, the frame rate, and the radiographing time that are more suitable radiographing conditions in dynamic radiographing can be set.

The radiographing console 2 according to this embodiment includes a second obtainer (controller 21) that obtains second order information that is information about the radiograph site, and the second determiner determines the second radiographing condition, based on the target image quality and the second order information.

Accordingly, more suitable radiographing conditions in dynamic radiographing can be set based on the target image quality and the second order information.

In the radiographing console 2 according to this embodiment, the second order information includes the BMI of the object.

Accordingly, more suitable radiographing conditions in dynamic radiographing can be set based on the BMI of the object, which is the second order information.

In the radiographing console 2 according to this embodiment, the second determiner determines the second radiographing condition, based on the second table that indicates the relationship between the target image quality and the second order information, and the second radiographing condition.

Consequently, a more suitable radiographing condition in dynamic radiographing can be easily set based on the second table.

In the radiographing console 2 according to this embodiment, the second radiographing condition includes any of a tube voltage, a tube current, and a radiation emission time per frame image in the radiation source. Consequently, the tube voltage, the tube current in the radiation source and the radiation emission time in each frame image that are more suitable radiographing conditions in dynamic radiographing can be set.

In the radiographing console 2 according to this embodiment, the first determiner determines the target signal value in the region of interest in the frame image or the target value of the indicator indicating the image quality, as the target image quality, based on the first order information, and the second determiner determines the second radiographing condition that can achieve the target signal value or the target value of the indicator indicating the image quality.

Consequently, the radiographing conditions that achieve the target signal value in the region of interest in the frame image, or the target value of the indicator indicating the image quality can be easily determined.

The radiographing console 2 according to this embodiment includes: a calculator (controller 21) that calculates the total dose during dynamic radiographing, based on the first radiographing condition determined by the first determiner and the second radiographing condition determined by the second determiner; a verifier (controller 21) that verifies whether the total dose calculated by the calculator is higher than a predetermined value; and a notification controller (controller 21) that issues an alert, if the total dose is verified to be higher than the predetermined value by the verifier.

Consequently, if the total dose is higher than a safe value less affecting the human body, the alert is issued, thus allowing the user to be notified.

The radiographing console 2 according to this embodiment includes a display controller (controller 21) that causes the display 24 to display a proposal for reducing a frame rate during the dynamic radiographing or reducing a radiographing time of the dynamic radiographing, if the total dose is verified to be higher than the predetermined value by the verifier.

Consequently, by adjusting the frame rate or the radiographing time so as to prevent the total dose from being higher than the safe value less affecting the human body, the radiographing conditions of safe dynamic radiographing less affecting the human body can be determined.

Although the embodiment of the present invention has been described above, note that the present invention is not limited to such an embodiment, and obviously various modifications are possible within a scope that does not depart from the gist of the present invention.

For example, in this embodiment, the case where the radiographing console 2 functions as the radiographing control apparatus is exemplified. However, the radiographing control apparatus is not limited thereto. For example, a configuration may be adopted where the diagnosis console 3 functions as the radiographing control apparatus.

In this embodiment, the distance (SID) between the radiation source 11 and the radiation detector 13, which is the radiographing condition A, is determined based on the presence or absence of dynamic analysis or the dynamic analysis item, which is the first order information. However, there is no limitation thereto. In a case where the radiographing system 100 is a visiting car, it may be configured so that a detector that detects the actual SID is provided, and the SID is determined based on a detection result of the detector.

In this embodiment, the radiographing posture, which is the radiographing condition A, is determined based on the presence or absence of dynamic analysis or the dynamic analysis item, which is the first order information. However, there is no limitation thereto. It may be configured so that determination is made based on another condition.

In this embodiment, the second order information is the BMI of the object. However, the information is not limited thereto. The second order information may be the height, weight, body thickness, and chest front/side as radiograph sites, of the object.

In this embodiment, in the radiographing condition table, the numerical value of BMI of the object is adopted as the minor category. However, there is no limitation thereto. The BMI level (underweight, normal weight, obesity degree 1, . . . ) may be adopted as the minor category.

In this embodiment, in the radiographing condition table, the BMI of the object is adopted as the minor category, and the BMI is classified into 10 or higher and less than 20, 20 or higher and less than 30, 30 or higher and less than 40, and 40 or higher. However, there is no limitation thereto. In the radiographing condition table, for the minor category, the BMI may be classified in increments of 1 (e.g., 10 or higher and less than 11), or classified in increments of 5 (e.g., 10 or more and less than 15).

The radiographing condition table is not limited to the examples shown in FIGS. 2 and 5.

The relationship between the S-value and the BMI of the patient as shown in FIG. 3A, or the relationship between the mAs value and the BMI of the patient as shown in FIG. 3B may be fed back to the radiographing condition table to be updated.

The temporal variation in actual radiation output with respect to the setting value due to deterioration of the radiation source 11 or the like may be reflected in the radiographing condition table.

The combination of the tube current and the pulse time in the radiographing condition B is not limited to the examples shown in FIGS. 2 and 5. As shown in FIG. 3B, the BMI of the patient and the mAs value have a correlation indicated by linear approximation. Accordingly, the combination of the tube current and the pulse time that can achieve the mAs value corresponding to the BMI of the patient can be freely set.

Based on the BMI of the patient, the mAs value may be calculated by an approximate expression, such as of linear approximation, polynomial approximation, or exponential approximation (logarithmic approximation), and the radiographing condition may be determined from the calculated mAs value.

In the examples shown in FIGS. 2 and 5, the applied filter uses Cu 0.2 mm. However, the applied filter is not limited thereto. If an applied filter is different, radiation quality (tube voltage) and dose (mAs value) are also different. Therefore, when a different applied filter (the filter type, filter thickness, etc.) is used, it is preferable to create a radiographing condition table based on the condition.

In radiographing by the radiographing system 100, radiation is emitted with no object being preliminarily arranged, in a predetermined radiographing condition serving as a reference, and a solid image (uniformly exposed image) to be read is radiographed. Based on the signal value of the radiation detector 13 in uniform exposure radiographing, the output of the radiation source 11 and the sensitivity of the radiation detector 13 are adjusted with respect to each other, thus performing calibration. Subsequently, the radiographing condition may be determined by the above radiographing condition determination process to perform radiographing. Preferably, the calibration of the radiation source 11 and the radiation detector 13 is performed at regular intervals (e.g., everyday, once a week, etc.).

In this embodiment, by the input operation of the user, the tube voltage value, the tube current value, the pulse time, the frame rate, and the radiographing time can be adjusted as shown in FIGS. 7 and 8, and the dynamic analysis item, the respiration protocol and the radiographing posture can be selected as shown in FIG. 8. However, there is no limitation thereto. It may be configured so that by an input operation of the user, the distance (SID) between the radiation source 11 and the radiation detector 13, or the target image quality can be adjusted. In a case where by an input operation of the user, the SID or the target image quality is changed from the value in the radiographing condition table, the radiographing condition B may be changed accordingly.

Furthermore, the detailed configuration of each of the components constituting the radiographing control apparatus (the radiographing console 2 in this embodiment) and the detailed operation can be appropriately changed in a range without departing from the spirit of the present invention.

Although embodiments of the present invention have been described and illustrated in detail, the disclosed embodiments are made for purposes of illustration and example only and not limitation. The scope of the present invention should be interpreted by terms of the appended claims.

The invention claimed is:

1. A radiographing control apparatus emitting radiation to an object and obtaining a plurality of frame images to control dynamic radiographing that radiographs dynamics of the object, the radiographing control apparatus comprising a hardware processor that:
    obtains first order information that includes at least one of information on presence or absence of dynamic analysis executed for a dynamic image obtained by the dynamic radiographing, and information on a dynamic analysis item;
    determines a first radiographing condition and a target image quality, based on the obtained first order information; and
    determines a second radiographing condition for achieving the determined target image quality.

2. The radiographing control apparatus according to claim 1, wherein the first order information includes instruction information about respiration of the object during the dynamic radiographing.

3. The radiographing control apparatus according to claim 1, wherein the hardware processor determines the first radiographing condition, based on a first table that indicates a relationship between the first order information and the first radiographing condition.

4. The radiographing control apparatus according to claim 1, wherein the first radiographing condition includes any of a posture of the object during the dynamic radiographing, a distance between a radiation source and a radiation detector that generates an image in accordance with radiation emitted from the radiation source, a frame rate during the dynamic radiographing, and radiographing time of the dynamic radiographing.

5. The radiographing control apparatus according to claim 1,
    wherein the hardware processor obtains second order information that is information about a radiograph site, and
    the hardware processor determines the second radiographing condition, based on the target image quality and the second order information.

6. The radiographing control apparatus according to claim 5, wherein the second order information includes a BMI of the object.

7. The radiographing control apparatus according to claim 5, wherein the hardware processor determines the second radiographing condition, based on a second table that indicates a relationship between the target image quality and the second order information, and the second radiographing condition.

8. The radiographing control apparatus according to claim 5, wherein the second radiographing condition includes any of a tube voltage, a tube current, and a radiation emission time per frame image in the radiation source.

9. The radiographing control apparatus according to claim 5,
    wherein the hardware processor determines a target signal value of a region of interest in the frame image, or a target value of an indicator indicating an image quality, as the target image quality, based on the first order information, and the hardware processor determines the second radiographing condition that can achieve the target signal value, or the target value of the indicator indicating the image quality.

10. The radiographing control apparatus according to claim 5,
wherein the hardware processor
calculates a total dose during the dynamic radiographing, based on the first radiographing condition determined by a first determiner, and the second radiographing condition determined by a second determiner,
verifies whether the calculated total dose is higher than a predetermined value, and
issues an alert, if the total dose is verified to be higher than the predetermined value.

11. The radiographing control apparatus according to claim 10,
wherein the hardware processor
causes a display to display a proposal for reducing a frame rate during the dynamic radiographing or reducing a radiographing time of the dynamic radiographing, if the total dose is verified to be higher than the predetermined value.

12. A radiographing system, comprising:
the radiographing control apparatus according to claim 5; and
an external apparatus that is connected to the radiographing control apparatus, and transmits the first order information and the second order information.

13. A non-transitory computer readable recording medium storing a program causing a computer of a radiographing control apparatus emitting radiation to an object and obtaining a plurality of frame images to control dynamic radiographing that radiographs dynamics of the object to perform:
obtaining first order information that includes at least one of information on presence or absence of dynamic analysis executed for a dynamic image obtained by the dynamic radiographing, and information on a dynamic analysis item;
determining a first radiographing condition and a target image quality, based on the obtained first order information; and
determining a second radiographing condition for achieving the determined target image quality.

* * * * *